United States Patent
Drysdale et al.

(10) Patent No.: US 7,355,050 B2
(45) Date of Patent: *Apr. 8, 2008

(54) (METH)ACRYLATE AMIDE ACETALS

(75) Inventors: Neville Everton Drysdale, Newark, DE (US); Laura Ann Lewin, Greenville, DE (US); Robert John Barsotti, Franklinville, NJ (US); Charles J. Brandenburg, Chesterfield, VA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 161 days.

This patent is subject to a terminal disclaimer.

(21) Appl. No.: 11/241,403

(22) Filed: Sep. 30, 2005

(65) Prior Publication Data
US 2006/0128774 A1  Jun. 15, 2006

Related U.S. Application Data

(60) Provisional application No. 60/615,362, filed on Sep. 30, 2004.

(51) Int. Cl.
*C07D 498/04* (2006.01)
(52) U.S. Cl. .................................................. 548/218
(58) Field of Classification Search .................. 548/218
See application file for complete search history.

(56) References Cited

U.S. PATENT DOCUMENTS

| | | | |
|---|---|---|---|
| 2006/0069204 A1* | 3/2006 | Drysdale et al. | 524/589 |
| 2006/0128774 A1* | 6/2006 | Drysdale et al. | 514/375 |
| 2006/0128873 A1* | 6/2006 | Drysdale et al. | 524/548 |

* cited by examiner

*Primary Examiner*—Rebecca Anderson
*Assistant Examiner*—Joseph R. Kosack

(57) ABSTRACT

The present invention, in one aspect, is a composition comprising (meth)acrylate amide acetals. Acetals of the present invention are useful as components in coatings for automotive and architectural structures. Coatings comprising components of the present invention cure rapidly with low VOC emissions. In another aspect, the present invention provides a process for making (meth)acrylate amide acetals described herein.

9 Claims, No Drawings

(METH)ACRYLATE AMIDE ACETALS

CROSS REFERENCE TO RELATED APPLICATION

This application claims the benefit of U.S. Provisional Application 60/615,362, filed Sep. 30, 2004.

FIELD OF THE INVENTION

The present invention relates to (meth)acrylate amide acetals which are readily prepared from the reaction of hydroxy amide acetals with methacryloyl chloride or via ester exchange reaction with methyl (meth)acrylate. This provides the monomers for eventual preparation of polymeric amide acetals.

BACKGROUND OF THE INVENTION

Amide acetals have been used for example in copolymerization with polyisocyanates as disclosed in U.S. Pat. No. 4,721,767. Cross-linked amide acetal based coating compositions dry and cure rapidly without the potential problems created by VOC emissions. Such coatings can be very useful, for example, in the automotive coatings industry.

Co-owned and co-pending US Patent Publication 2005-007461 describes polymeric compositions containing amide acetal groups, which are crosslinked by hydrolyzing the amide acetal groups, and subsequently reacting the hydroxyl groups and/or the amine functions that are formed to crosslink the composition.

Co-owned and co-pending U.S. patent application Ser. No. 10/960,656 describes a catalytic process for making amide acetals from nitriles and diethanolamines.

CA 132: 280540, an anonymous disclosure, alluded to the potential preparation of hydroxy amide acetals from epoxides and oxazolines but did not include how to make these, nor provide any experimental results.

SUMMARY OF THE INVENTION

The present invention relates to (meth)acrylate amide acetal compositions of the formula

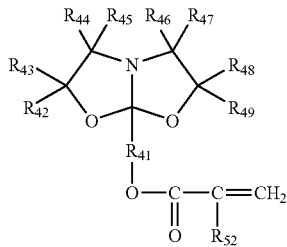

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group;

$R_{52}$ is hydrogen or methyl; and n is 1-10.

It further relates to the process to form (meth)acrylate amide acetals, said process comprising reacting a hydroxy amide acetal of the formula

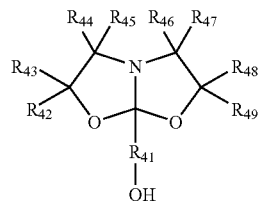

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and n is 1-10;

with an ester of the formula

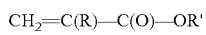

$$CH_2{=}C(R){-}C(O){-}OR'$$

where R is hydrogen or methyl and R' is $C_1$-$C_{20}$ alkyl.

The invention further relates to a process for forming a (meth)acrylate amide acetals, said process comprising reacting a hydroxy amide acetal of the formula

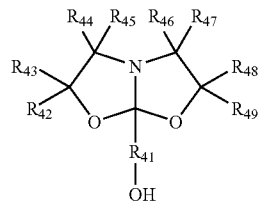

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and n is 1-10;

with an acid halide, such as

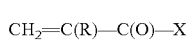

$$CH_2{=}C(R){-}C(O){-}X$$

where X is a halogen selected from the group consisting of Cl, and Br; R is hydrogen or methyl; said reaction performed in the presence of a base selected from the group consisting of triethylamine and pyridine.

The present invention further relates to a process for forming a (meth)acrylate amide acetal, said process comprising reacting a hydroxy amide acetal of the formula

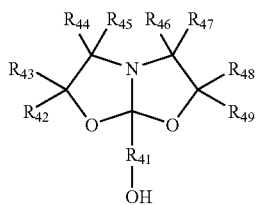

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and n is 1-10;

with an (meth)acrylic anhydride of the formula

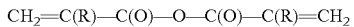

where each R is independently methyl or ethyl, said reaction performed in the presence of a base selected from the group consisting of triethylamine and pyridine.

The present invention further relates to products formed by the disclosed processes.

DETAILS OF THE INVENTION

The present invention relates to a process for the preparation of (meth)acrylate amide acetals. Amide acetals have the general formula

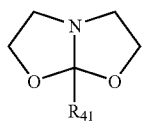

General processes for producing amide acetals are disclosed in co-owned and co-pending U.S. Patent Publication 2005-007461 and U.S. patent application Ser. No. 10/960,656). As disclosed in these applications, amide acetals can also be represented by the formula

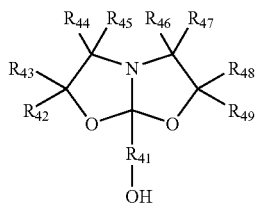

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino; and $R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and where n is 1-10. It is more typical that $R_{42}$-$R_{49}$ each independently represent hydrogen and $C_1$-$C_{10}$ alkyl groups.

The amide acetal as shown above is used to produce (meth)acrylate amide acetals by any of several methods, including transesterification and reaction with an acid halide in the presence of a base. With transesterification, the amide acetal would react with an ester such as

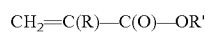

where R is hydrogen or methyl and R' is $C_1$-$C_{20}$ alkyl. Reaction with an acid halide, such as

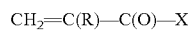

or a (meth)acrylate anhydride

where each R is independently hydrogen or methyl and X is a halogen such as Cl or Br, in the presence of a base (e.g., triethylamine, pyridine) also gives the desired end-product. The formula for these (meth)acrylate amide acetals is

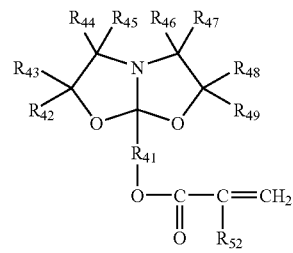

where $R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and $R_{52}$ is either hydrogen or methyl.

Generally, for the transesterification method, an excess of the methyl or ethyl (meth)acrylate is mixed with the hydroxy amide acetal together with a catalytic amount of a base, such as titanium (IV) butoxide. The reaction mixture is heated and the liberated methanol or ethanol is removed. Vacuum distillation affords the desired product.

Generally, for the acid halide or anhydride method, the hydroxy amide acetal and a base, such as pyridine or triethylamine, are mixed with an organic solvent such as tetrahyrofuran or dichloromethane. The resulting solution is cooled to 0° C. under nitrogen. The acid halide or (meth) acrylate anhydride is then slowly added. After completion of the reaction the salts are removed via filtration and vacuum distillation affords the desired material.

The materials made by the process described find use in a variety of end-uses, including but not limited to components in coatings for automotive and architectural structures.

These and other features and advantages of the present invention will be more readily understood, by those of ordinary skill in the art, from a reading of the following detailed description. It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both preceded by the word "about." In this manner slight variations above and below the stated ranges can be used to achieve substantially the same results as values within the ranges. Also, the disclosure of these ranges is intended as a continuous range including every value between the minimum and maximum values.

Unless otherwise stated, all chemicals and reagents were used as received from Aldrich Chemical Co., Milwaukee, Wis.

EXAMPLES

Example 1

2-Methyl-acrylic acid 5-(2,6-dimethyl-tetrahydro-oxazolo[2,3-b]oxazol-7a-yl)-pentyl ester

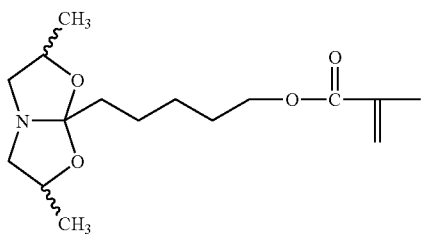

In an oven dried 100 mL round-bottom flask equipped with a pressure equalizing addition funnel and a reflux condenser were added 5-(2,6-Dimethyl-tetrahydro-oxazolo [2,3-b]oxazol-7a-yl)-pentan-1-ol (22.9 g, 0.01 mol) followed by chloroform 50 mL and triethylamine 12.12 g, 0.12 mol). The reaction content was cooled to 0° C. under nitrogen. While stirring a solution of methacryloyl chloride (11.44 g, 0.11 mol) in chloroform was added slowly. After completion of the acid chloride the reaction was stirred one hour at 0° C., then allowed to warmed to room temperature and then stirred over night at room temperature. The triethylamine salt was filter off through Celite® (World Minerals, Santa Barbara, Calif.), the filtrate concentrate at reduced pressure. NMR (proton) showed this material to be the desired material contaminated with triethyl amine salt. This material was then washed with hexanes (2×125 ml), the hexanes washes combined concentrated giving 13.74 g of product.

Example 2

2-Methyl-acrylic acid 2,6-dimethyl-tetrahydro-oxazolo[2,3-b]oxazol-7a-ylmethyl ester

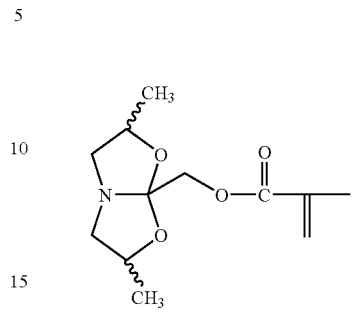

In an oven dried 300 mL round-bottom flask equipped with a reflux condenser were added 2,6-Dimethyl-tetrahydro-oxazolo[2,3-b]oxazol-7a-yl-methanol (789 g, 0.45 mol), methyl methacrylate (180.0 g, 1.80 mol), Prostab® 5415 (3.00 g, Ciba Specialty Chemicals, Basel, Switzerland) and titanium (iv) n-butoxide (6.00 g, 0.024 mol). The reaction content was heated to 110° C. for ~8 hours GC analyses indicated ~44% conversion. The reflux condenser was replaced with an oven dried distillation head and the distillate boiling between 60-70° C. collected. The distillation head was replaced with a reflux condenser and the reaction content heated to 120° C. for ~4 hours, at the end of which GC analyses indicated the conversion to be ~75%. Again the reflux condenser was replaced with a distillation head and the distillated boiling between 60-70° C. collected for ~8 hours, at the end of which GC analyses indicated the conversion to be ~90%. The reaction content was cooled to room temperature and the unreacted methyl methacrylate removed under vacuum and then the remaining reaction content vaccuum fractionally distilled affording four fractions:

| Fraction | Head Temp (° C.) | Pot Temp (° C.) | Vacuum (torr) | Weight (g) | Comments |
|---|---|---|---|---|---|
| 1 | 85 | 122 | 1.5 | | |
| 2 | 85-94 | 120 | 1.4 | | |
| 3 | 94-96 | 122 | 1.3 | 8.55 | some product |
| 4 | 96-105 | 122-140 | 1.3-1.1 | 58.45 | Almost all product (GC~92%) |

What is claimed is:

1. An (meth)acrylate amide acetal composition of the formula

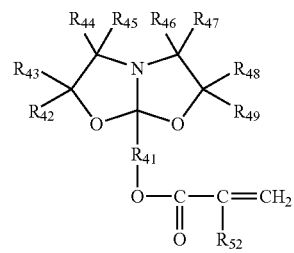

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and $R_{52}$ is hydrogen or methyl; and n is 1-10.

2. The (meth)acrylate amide acetal of claim 1, wherein $R_{42}$-$R_{49}$ each independently represent hydrogen and $C_1$-$C_{10}$ alkyl groups.

3. A process for forming a (meth)acrylate amide acetal, said process comprising reacting a hydroxy amide acetal of the formula

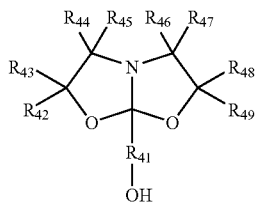

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and n is 1-10;

with an ester of the formula

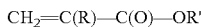

where R is hydrogen or methyl, and R' is $C_1$-$C_{20}$ alkyl; in the presence of a catalytic amount of base.

4. The process of claim 3, wherein $R_{42}$-$R_{49}$ each independently represent hydrogen and $C_1$-$C_{10}$ alkyl groups.

5. A process for forming a (meth)acrylate amide acetal, said process comprising reacting a hydroxy amide acetal of the formula

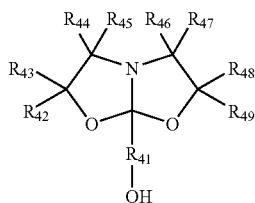

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and n is 1-10;

with an acid halide, such as

where X is a halogen selected from the group consisting of Cl and Br; R is hydrogen or methyl; said reaction performed in the presence of a base selected from the group consisting of triethylamine and pyridine.

6. The process of claim 5, wherein $R_{42}$-$R_{49}$ each independently represent hydrogen and $C_1$-$C_{10}$ alkyl groups.

7. A process for forming a (meth)acrylate amide acetal, said process comprising reacting a hydroxy amide acetal of the formula

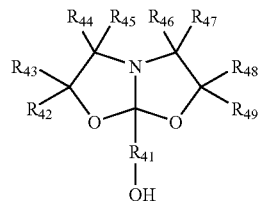

wherein $R_{42}$-$R_{49}$ independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$, wherein $R_{50}$ and $R_{51}$ are each independently represent a hydrogen, $C_1$-$C_{20}$ alkyl, $C_2$-$C_{20}$ alkenyl, $C_2$-$C_{20}$ alkynyl, $C_6$-$C_{20}$ aryl, $C_2$-$C_{20}$ alkyl ester, or $C_7$-$C_{20}$ aralkyl group; and n is 1-10;

with a (meth)acrylic anhydride of the formula

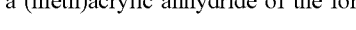

where each R is independently hydrogen or methyl, said reaction performed in the presence of a base selected from the group consisting of triethylamine and pyridine.

8. The process of claim 6, wherein $R_{42}$-$R_{49}$ each independently represent hydrogen and $C_1$-$C_{10}$ alkyl groups.

9. A product of the process of any of claims 3-8.

* * * * *